(12) United States Patent
Funck et al.

(10) Patent No.: US 7,319,934 B2
(45) Date of Patent: Jan. 15, 2008

(54) METHOD AND DEVICE FOR DETERMINING THE ACOUSTIC PARAMETERS OF FLUIDS IN A RESONATOR DEVICE

(75) Inventors: Theodor Funck, Gottingen (DE); Leo De Maeyer, Gottingen (DE)

(73) Assignee: TF Instruments GmbH, Heidelberg (DE)

( * ) Notice: Subject to any disclaimer, the term of this patent is extended or adjusted under 35 U.S.C. 154(b) by 102 days.

(21) Appl. No.: 10/485,431

(22) PCT Filed: Jul. 29, 2002

(86) PCT No.: PCT/EP02/08433

§ 371 (c)(1),
(2), (4) Date: Sep. 9, 2004

(87) PCT Pub. No.: WO03/014723

PCT Pub. Date: Feb. 20, 2003

(65) Prior Publication Data

US 2005/0043906 A1    Feb. 24, 2005

(30) Foreign Application Priority Data

Aug. 1, 2001 (DE) .............................. 101 37 679

(51) Int. Cl.
*G01N 31/00* (2006.01)
*G01N 11/00* (2006.01)

(52) U.S. Cl. ................................... 702/54; 702/23

(58) Field of Classification Search ................ 702/54, 702/22–25, 30, 50.1, 37
See application file for complete search history.

(56) References Cited

U.S. PATENT DOCUMENTS

| 4,862,384 A | * | 8/1989 | Bujard et al. | ................. 702/54 |
| 6,216,091 B1 | * | 4/2001 | Hammond | ................... 702/23 |
| 6,644,119 B1 | * | 11/2003 | Sinha | .......................... 73/579 |

* cited by examiner

*Primary Examiner*—John Barlow
*Assistant Examiner*—Jonathan Moffat
(74) *Attorney, Agent, or Firm*—Caesar, Rivise, Bernstein, Cohen & Pokotilow, Ltd.

(57) ABSTRACT

A method for determining acoustic parameters of a liquid (1) in a resonator arrangement having a resonator chamber (2) includes the following steps: acoustic excitation of the liquid in the resonator chamber (2) in such a way that a sequence of liquid resonances is excited in a frequency range in which the wall material of the resonator chamber (2) and/or associated transducers (6) have natural resonances with amplitude different from zero, and measurement of the associated resonance frequencies of the liquid in the resonator chamber (2); determining an observed deviation of the measured resonance frequencies from ideal resonance frequencies in an ideal resonator corresponding to the resonator chamber (2); calculating a simulation function ($y_k$), which is a function of the acoustic parameters of the liquid (1) and represents calculated deviations of the resonance frequencies from the ideal resonance frequencies; adapting the calculated deviations to the observed deviations through variation of the acoustic parameters of the simulation function ($y_k$); and deriving the acoustic parameters sought from the adapted simulation function ($y_k$). A resonator arrangement for implementing the method is also described.

9 Claims, 2 Drawing Sheets

METHOD AND DEVICE FOR DETERMINING THE ACOUSTIC PARAMETERS OF FLUIDS IN A RESONATOR DEVICE

BACKGROUND OF THE INVENTION

The present invention relates to methods for determining acoustic parameters of liquids in an acoustic resonator, particularly a method for determining absolute acoustic values of the liquids from a sequence of acoustic liquid resonances, and a resonator arrangement for performing a method of this type.

The characterization of liquids on the basis of their acousto-mechanical properties using an acoustic resonator is generally known. An acoustic resonator is a container, whose shape is dependent on its application, in which a quantity of liquid is excited to mechanical oscillations which are reflected as sound waves between two diametrically opposite walls of the container. The excitation is performed using electrical or magnetic elements (electroacoustic or magnetoacoustic transmitters), which are acoustically coupled to the container. The liquid oscillations have resonances at certain frequencies, the reflected sound waves interfering with one another in such a way that they amplify to a spatial standing wave. The resonance frequencies depend on the shape and the composition (e.g., material, surface properties) of the container and of the properties of the liquid to be investigated in the resonator. The resonance frequencies are determined, for example, by detecting electrical measured variables (e.g., current, voltage) at the transmitter or by detecting the oscillation amplitudes using acoustically coupled receiver elements.

Numerous techniques are known for oscillation excitation, oscillation measurement, and analysis of the frequency characteristic of the liquid. For example, in WO 94/24526 an ultrasonic measurement device having a non-piezoelectric resonator chamber body and electroacoustic transducers positioned on its outside is described. The inner walls of the resonator chamber body form a resonator being as ideal as possible for generating standing linear sound waves in the liquid. For this purpose, the resonator chamber body must be produced with special precision. In addition, the most effective possible coupling of the external electroacoustic transducers to acoustically conductive layers is provided. The area of application of the conventional ultrasonic measurement device is restricted because of the complex construction of the resonator chamber body.

A method for evaluating acoustical-electrical measured variables to obtain acoustic parameters or variables derived therefrom is known from WO 95/12123. This method requires performing comparative measurements using a measurement resonator, which is filled with a liquid sample, and a reference resonator, which contains a known liquid. The performance of reference measurements is disadvantageous since they represent an additional measurement outlay and possibly impair the precision of the measured variable analysis.

A measurement method using acoustic standing cylinder waves is known from U.S. Pat. No. 5,533,402. This technology also has the disadvantage that reference measurements must be performed to obtain acoustic parameters. A further disadvantage relates to the cylinder resonators described in U.S. Pat. No. 5,533,402, which must again be produced with high precision to generate the cylindrical waves.

Cylinder resonators having curved electroacoustic transducers are known from the book "Ultrasonic Interferometers" by V. Ilgunas et al., (Russian language, Verlag Mokslas, Vilnius 1983). Using these resonators, standing wave fields may be generated whose resonances have a constant frequency interval. The frequency interval is nearly a linear function of the mutual spacing of the curved transducers. To avoid cylindrical resonances, the resonators are constructed as open resonators. This is disadvantageous since the transducers must be dipped into the sample liquid. A closed sample chamber is not produced.

Physical formulas are also known for theoretically calculating liquid resonances in ideal resonators. In these formulas, which are described below, some real conditions of the acoustic excitation, particularly the inclusion of the natural resonance of the transducer used for the excitation on the observed resonance frequencies of the liquid, are not taken into consideration (see J. P. M. Trusler in "Physical Acoustics and Metrology of Fluids", Adam Hilger Verlag, Bristol, Philadelphia, New York, 1991, pp. 52–89).

The object of the invention is to provide improved methods and devices for determining acoustic parameters and/or values of liquids derived therefrom, using which the disadvantages of the conventional techniques are avoided. In particular, acoustic characterization of the liquids with increased precision is to be made possible, without a reference measurement being necessary. The method is also to be implementable using a simplified resonator construction.

SUMMARY OF THE INVENTION

The present invention is based on the idea of exciting acoustic oscillations of the liquid to be investigated in a resonator, which are coupled to oscillations of at least one further resonator made of solid material, so that a joint oscillation spectrum is formed, and determining acoustic properties of the liquid, such as the speed of sound in the liquid, the acoustic impedance, the density, and possibly viscoelastic properties of the liquid, from the joint oscillation spectrum near the natural frequency of the at least one further resonator. In this case, the natural frequency of the coupled solid resonator is to be at least 10 times higher than the lowest frequency (basic frequency) of the first (liquid) resonator. The frequency spectrum of the coupled oscillations includes a sequence of resonance frequencies having sequential (or increasing or decreasing) harmonic orders. The inventors have determined that the resonance frequencies in the range of the natural frequency of the coupled (solid) resonator deviates strongly in a predetermined way from the linear harmonic sequence of an ideal, non-coupled resonator. The desired acoustic properties of the liquid may advantageously be determined from the deviation.

A wall of the resonator arrangement which is set up for the purpose of implementing oscillations at a predetermined excitation frequency may be used as the coupled resonator made of a solid material. Alternatively, an electroacoustic transducer may also be used as the solid resonator, which is coupled to the (liquid) resonator and is operated in the range of its natural frequency.

The deviations of the resonance frequencies of the coupled oscillations from the resonance frequencies in the ideal resonator are analyzed, using a simulation function, to characterize the coupling between the two resonators. The desired acoustic properties of the liquid result in the way described below from the simulation function. Besides the acoustic properties of the liquid sought, known or empirically determined properties of the coupled solid resonator are also entered in the simulation function. The simulation function is thus produced in dependence on the concrete application, e.g., on the basis of an analysis of the resonator behavior or empirically. The properties of the solid resonator advantageously do not change, in contrast to the properties of the liquid to be measured, so that the real coupled resonance system indirectly fulfills the function of a reference oscillator having a reference spectrum.

A resonator arrangement according to the invention for characterizing acoustic properties of a liquid particularly includes a resonator chamber for receiving the liquid and at least one sound transducer, which is attached to the resonator chamber, the sound transducer touching the resonator chamber and/or the liquid from the outside. The sound transducer is operated in a predetermined range of excitation frequencies, which includes the natural resonance, for example, of the thickness oscillation of a wall in contact with the liquid, which reflects the sound waves in the liquid.

The resonator chamber forms a container for the liquid to be investigated. Depending on the structural shape, the material, which is capable of natural oscillations, is touched by the liquid, and reflects the sound waves, is formed by the active sound transducer itself, or it is excited from outside by the sound transducer in the range of the natural oscillations, whose frequency is to be much higher than the differential frequency of two sequential resonance frequencies of the liquid. The inner transducer or wall surface in the resonator chamber is referred to in the following in general as the inner wall.

In the conventional methods described above, exciting resonances other than the pure liquid resonances in the resonator is avoided at great expense. The conventional resonator arrangements are designed in such a way that as little coupling of oscillation elements which lie outside the liquids as possible occurs. Therefore, care must particularly be taken to analyze only a few undisturbed liquid resonances, whose frequencies are influenced as little as possible by the natural frequency of the transducer used for the excitation. In contrast, the present invention is based precisely on using the natural influence of the resonator behavior by at least one coupled external resonance for this purpose to obtain additional information about the acoustic liquid properties.

The analysis of the deviation of the frequency properties of a sequence of liquid resonances from the ideal behavior has the advantage that a resonator arrangement having a simplified construction may be used. In addition, it is of special advantage that in the method according to the present invention, reference measurements may be dispensed with. Since, in the method according to the present invention, precisely the real behavior of the oscillation excitation is analyzed, interfering influences, such as gas bubble formation, are compensated for.

BRIEF DESCRIPTION OF SEVERAL VIEWS OF THE DRAWINGS

Further advantages and details of the present invention are apparent from the description of the attached drawings.

DETAILED DESCRIPTION OF PREFERRED EMBODIMENTS OF THE INVENTION

Theoretical Foundations

Figure 1:
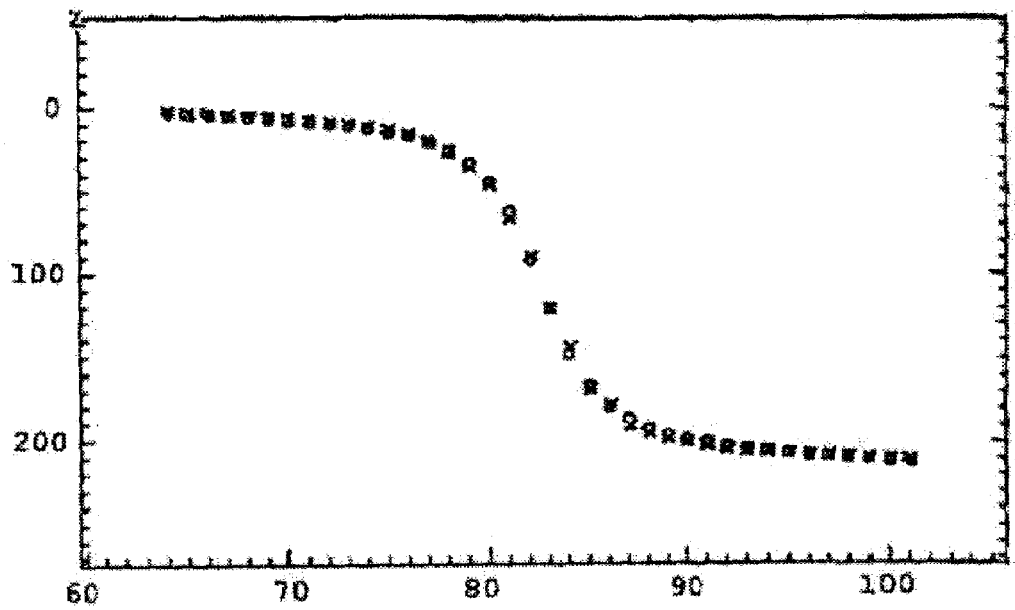
FIG. 1 shows a curve of a sequence of resonance frequencies in a plane resonator.

The resonance frequencies of a liquid form a harmonic series, in which the individual resonance frequencies are related to one another according to a simple and physical law, under ideal conditions only. The ideal conditions would include, for example, an infinitely extended plane of the wave propagation or a 100% reflection on the transducer surfaces. Under real conditions, however, the measured resonance frequencies of a liquid deviate from the ideal harmonic series.

This deviation is caused by the phase difference between the sound waves incident on an inner wall (transducer or chamber wall surface) and the reflected sound waves. The phase difference results from the difference between the complex acoustic impedance of the liquid and the impedance of the inner wall. The acoustic impedance is the ratio between sound pressure and local speed of the mass displacement. In the event of resonance, both variables are in phase, so that the imaginary part of the complex impedance disappears. The sound wave incident from the liquid partially penetrates into the adjoining material of the inner wall if this material does not have infinite impedance, and is partially reflected in further adjoining material layers and/or at the coupled acoustic transducers. The incident sound pressure shifts the container wall and thus periodically changes its geometry. A liquid resonance is given when the superposition of incident and reflected waves leads to a maximum overall amplitude of the standing sound wave in the liquid. This is the case when the imaginary part of the complex impedance (or the phase shift between reflected and continuing waves) disappears at the boundary surface between liquid and inner wall.

An important consideration of the inventors is that the deviations between the resonance frequencies actually observed and the resonance frequencies in an ideal container having infinitely rigid geometric shape and infinitely high impedance are especially large near the natural resonance of the container and/or of coupled mechanical resonators or transducers. This is taken into consideration in the construction and/or in operation of resonator arrangements according to the invention (see below).

For a given geometrical shape, layer thickness, and material composition of the walls of a resonator arrangement, the walls have a specific acoustic impedance. The phase differences cited and liquid resonance frequencies thus established are then also determined by the sound wavelength and the acoustic impedance of the liquid. In the ideal resonator, in contrast, the resonance frequencies are determined only by the ratio of the wavelength to the geometrical dimensions of the container. The acoustic impedance of the liquid plays no role in this case, if the acoustic impedance of the walls of the resonator may ideally be set equal to zero or infinite. Since the sound wavelength $\lambda$ is determined only by the speed of sound $c_L$ at a predetermined frequency f, the resonance frequencies in the ideal resonator may be calculated using known physical formulas, depending on geometry. For example, for a plane liquid layer of thickness D in a plane resonator arrangement, a harmonic sequence of the resonance frequencies results, the resonance of order n in the sequence being given by:

$$f_n = c_L/2nD \quad (1).$$

Therefore, under ideal conditions, the speed of sound in the liquid may be calculated from measured liquid resonances. Under real conditions, the error occurring is generally small if a very good approximation of the resonator arrangements used to the ideal geometry is ensured and the excitation is performed in frequency ranges which avoid coupling to specific resonances of the resonator arrangement (wall material and/or transducer resonances). This is exploited in the conventional acoustic measurements.

In principle, the speed of sound may be determined from the precise measurement of only one single resonance frequency, since all ideal resonances depend on only the speed of sound in a mathematically unique way. However, since the harmonic order n of the resonance measured is initially unknown, particularly for higher harmonic orders, in general two neighboring harmonic resonances are determined, and an approximate value of the basic frequency is determined from the difference of the resonance frequencies. The harmonic order results from the ratio of the resonance frequency and the basic frequency. To determine the harmonic order, the quotient of the resonance frequency and the basic frequency is rounded down to the closest whole number n. The number of half waves in the standing wave figure of the relevant resonance results. Using n and the known distance D between the reflecting walls, the wavelength is obtained from $$D = 2n\lambda \quad (2)$$

and finally the speed of sound in the liquid is obtained from $$c_L = \lambda f_n \quad (3).$$

However, the value of the speed of sound $c_L$ obtained is subject to error, since the measured resonance frequency deviates from the ideal harmonic frequency and the end nodes of the standing wave figure are not exactly coincident with the reflecting walls of the resonator arrangement.

In contrast to the conventional method, according to the present invention, the deviation of the measurable resonance frequencies for a specific geometry of the resonator from the resonance frequencies of an ideal resonator is exploited. The deviations are especially strong near a natural resonance of the reflecting structure. This is illustrated in FIG. 1.

Figure 3:
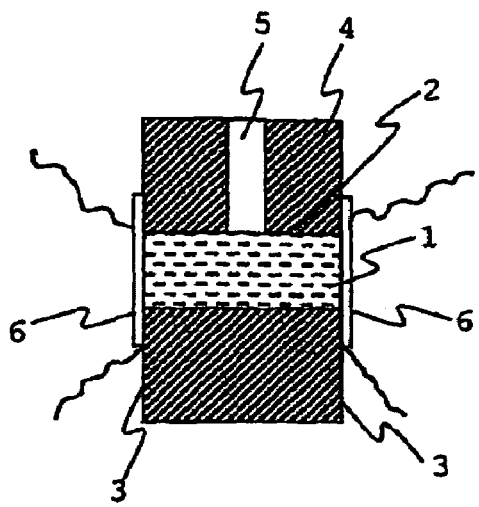
FIG. 3 shows a first embodiment of a resonator arrangement according to the invention.

FIG. 1 shows the difference between the theoretical harmonic resonance frequencies of an ideal resonator having the given plane liquid layer thickness D and the actual resonance frequencies measured in a resonator as shown in FIG. 3 as a function of the particular harmonic order. The measured resonances are indicated by crosses. For low harmonic orders, the resonance frequencies observed differ little at first, but then differ measurably from the theoretical harmonic series. With increasing harmonic order, the deviation increases strongly when the sequence of the measured frequencies passes through the natural resonance of the exciting transducer (middle part of the curve). At a greater distance from the natural resonance, the deviation is again approximately constant and reaches a value which corresponds to approximately double the basic frequency of the theoretical harmonic sequence.

Figure 4:
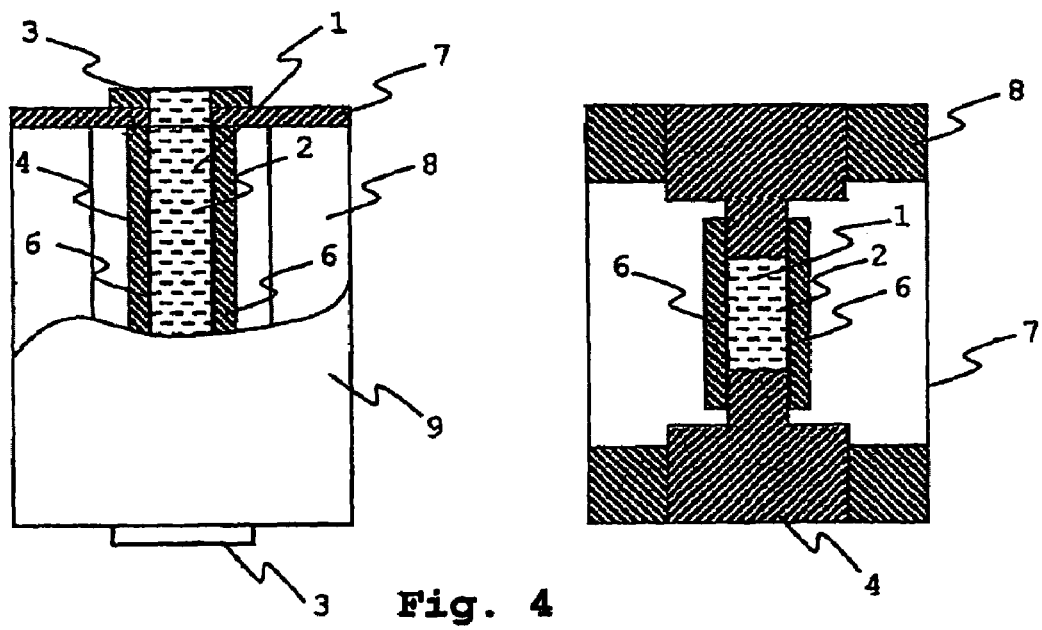
FIG. 4 shows a second embodiment of a resonator arrangement according to the invention.
Figure 5:
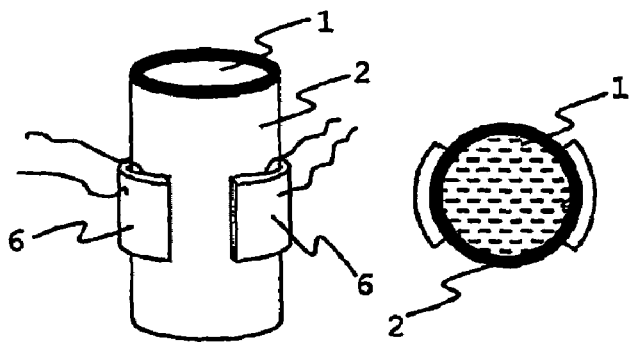
FIG. 5 shows a third embodiment of a resonator arrangement according to the invention.

The circles entered in FIG. 1 correspond to the values of the deviation calculated using a simulation function. In the simulation function used according to the invention, the ideal harmonic orders, and, as material variables, the speed of sound and the acoustic impedance of the liquid, the acoustic impedance of the reflecting wall material, and the resonance frequency of the wall material and/or of the coupled sound transducer are particularly entered. A simulation function for the embodiments of the resonator arrangement according to the invention illustrated in FIGS. 3 through 5 is specified in detail below.

The method on which the present invention is founded is now based on measuring a sequence of resonance frequencies of the liquid in the neighborhood of a natural resonance of the reflecting structure of the resonator arrangement and determining the coefficients occurring in the simulation function using a compensation calculation. In this case, the speed of sound is particularly determined absolutely and the acoustic impedance of the liquid is also determined. This represents a special advantage over the conventional methods for determining the speed of sound from the resonance frequency of an assumed ideal resonator.

Preferred Embodiments of Methods According to the Invention

To determine acoustic parameters of a liquid (sample) to be investigated according to the invention, first a measurement of a sequence of multiple liquid resonance frequencies in an acoustic resonator is performed. The resonator is formed, for example, by one of the resonator arrangements described below. The resonator is operated in the neighborhood of the natural resonance of the reflecting structure or the natural resonance of the sound transducer used. The frequency of the natural resonance is, for example, in the range from 8 to 10 MHz. The neighborhood of the natural resonance of interest is, for example, the range between $f_E/1.5$ and $1.5 f_E$. Depending on the embodiment, the width of this frequency range may be 6 MHz or more. As a result of this first method step, there is a sequence of resonance frequency values $f_k$ (e.g., 38 $f_k$ values).

Figure 2:
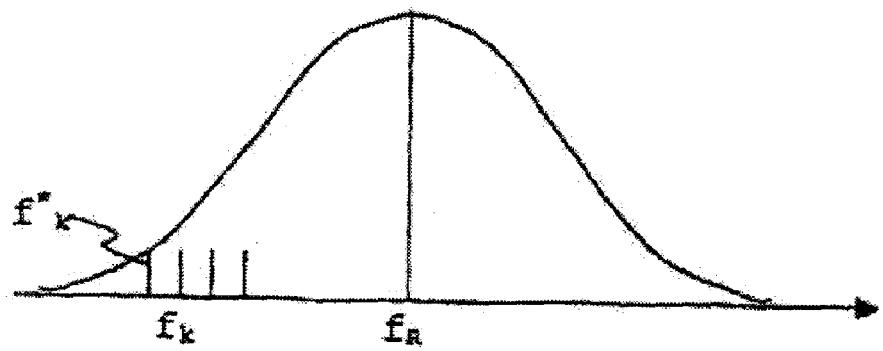
FIG. 2 shows a curve to illustrate the excitation of liquid resonances.

In a second step, the approximated basic frequency in an ideal resonator of the corresponding geometry is determined from the average frequency differential of the neighboring resonance frequencies in the part of the frequency range of the wall material which is furthest below the natural resonance $f_E$ of the wall material. For example, 18 resonance frequency values $f_k$ in the lower part of the frequency range are determined (see FIG. 2), the frequency differentials are calculated, and an average frequency differential is determined.

The basic frequency determined from the average frequency differential is below the basic frequency in the ideal resonator, since the frequencies observed and their differences are lower than the particular ideal harmonic frequencies.

In a next step, the integral harmonic order of the resonance frequency closest to the ideal resonator is determined. The quotient of the lowest measured resonance frequency $f_k^*$ (see FIG. 2) divided by the approximated basic frequency is determined. Since the basic frequency would be determined too low because of the deviations cited, the calculated quotient, which is non-integral, is above the corresponding ideal harmonic order. The desired integral harmonic order is therefore determined as the next higher whole number from the quotient determined.

Subsequently, the sequential measured resonance frequencies are numbered from the lowest measured frequency $f_k^*$ upward, beginning with the ideal harmonic order of the lowest resonance frequency determined in the preceding step. For each measured resonance frequency, the deviation between the observed resonance frequency and the resonance frequency calculated for the ideal resonator having the equal harmonic order is determined. This deviation is referred to as the observed deviation.

Finally, a simulation function $y_k$ is calculated which describes a calculated deviation from the ideal behavior. A function suitable for resonator arrangements as shown in FIGS. 3 through 5 is as follows:

$$y_k = \frac{c_L}{2D}\left\{k + \frac{2}{\pi}\arctan\frac{z_L}{z_R\tan\left\{\pi\frac{f_k}{f_R}\right\}}\right\} \text{ for } f_k < f_R \quad (4)$$

and $$y_k = \frac{c_L}{2D}\left\{k - 2 + \frac{2}{\pi}\arctan\frac{z_L}{z_R\tan\left\{\pi\frac{f_k}{f_R}\right\}}\right\} \text{ for } f_k > f_R \quad (5)$$

In these equations:
D layer thickness of the liquid
k harmonic order
$f_k$ observed resonance frequency
$f_R$ coupled resonance frequency of the reflecting wall structure
$c_L$ speed of sound in the liquid
$z_L$ acoustic impedance of the liquid
$z_R$ acoustic impedance of the reflecting wall
$y_k$ calculated deviation.

The parameters $c_L$, $f_L$, $z_L$, $z_R$, and $f_R$ occurring in the simulation function are determined through iterative minimization of the quadratic difference of the calculated deviation $y_k$ from the actual observed deviation. Already known variables such as D, $z_R$, and $f_R$ may be kept constant during the non-linear adaptation. It is to be emphasized that the implementation of the invention is not restricted to the simulation function cited here. Rather, the simulation function may also be altered as a function of the actual resonator used.

After adaptation of the calculated deviation to the observed deviation, the speed of sound in the liquid and the acoustic impedance are thus advantageously provided directly. From these variables, the density of the liquid or viscoelastic properties may be determined according to methods known per se (see, for example, A. J. Matheson in "Molecular Acoustics", Wiley-Interscience, London, New York, Sydney, Toronto, 1971, p. 76 et seq.).

The method steps cited may be repeated multiple times and the desired parameters of the liquid may be derived through averaging over the parameters obtained during the particular repetitions. The number of repetitions may be, for example, 9.

The simulation function corresponding to the equations (4) and (5) applies for resonator structures as shown in FIGS. 3 through 5, which are characterized by an approximately plane soundwave propagation in the liquid layer. The implementation of the invention is not restricted to the simulation function cited. For other resonator structures, simulation functions adapted to them may be used. Adapted simulation functions are empirically determined by measuring resonance liquids having known acoustic properties. As a function of the application, modification of the simulation function (4, 5) by adding empirical correction terms may also be provided for resonator structures having plane soundwave propagation. The empirical correction terms are also determined through comparative measurements using reference liquids having known acoustic properties in order to improve the adaptation precision for specific resonator structures or properties. Additional empirical terms may be taken into consideration according to the following equations (6, 7), for example. The correction factor introduced in equations (6, 7) may first be neglected (i.e., set to zero) for an iterative method. If necessary, an iteration using varied g while keeping $z_L$ and $f_R$ constant may then be performed.

$$y_k = \frac{c_L}{2D}\left\{k + \frac{2}{\pi}\arctan\frac{z_L}{z_R\tan\left\{\pi\frac{f_k}{f_R}[1 + g(f_k - f_R)]\right\}}\right\} \text{ for } f_k < f_R \quad (6)$$

and/or $$y_k = \frac{c_L}{2D}\left\{k - 2 + \frac{2}{\pi}\arctan\frac{z_L}{z_R\tan\left\{\pi\frac{f_k}{f_R}[1 + g(f_k - f_R)]\right\}}\right\} \text{ for } f_k > f_R. \quad (7)$$

The simulation functions (4–7) may also be applied for resonator structures having non-plane inner walls of the resonator chamber, if the excitation frequency of the sound transducer is especially high (e.g., 20 times higher than the basic frequency of the liquid resonance), particularly if a large distance from the natural frequency of the resonator chamber is selected. The inventors have determined that at high excitation frequencies in a resonator having diametrically opposite semicylindrical transducers, for example, an essentially plane soundwave propagation is surprisingly given, which allows an application of the simulation function (4, 5).

Preferred Embodiments of Resonator Arrangements According to the Invention

The methods described are implemented using resonator arrangements designed for exciting acoustic liquid resonances in a frequency range which is near a natural resonance of the inner wall of the resonator chamber reflecting the sound waves or includes this frequency. In this case, various designs are possible, three embodiments of which are illustrated for exemplary purposes in FIGS. 3 through 5.

A first embodiment of a resonator arrangement according to the present invention is shown in FIG. 3. The arrangement is formed by a solid, one-piece chamber body 4 having lateral plane-parallel end surfaces 3, between which a cylindrical hole 2 extends. The hole 2 is aligned in such a way that the cylinder axis is perpendicular to the end surfaces 3. The hole 2 forms the actual resonator chamber for receiving the liquid sample 1. To introduce or replace the liquid, at least one lateral channel 5 is provided in the chamber body 4. At the end surfaces 3, the resonator chamber 2 is terminated on both sides by piezoacoustic transducers 6, which press against the end surfaces 3 of the chamber body 4 on both sides and preferably are identical. The thickness of the piezoelectric transducers 6 is selected according to the invention in such a way that their natural resonance is at the same frequency in each case. Furthermore, both transducers 6 are produced from the same material, so that their acoustic impedance is also identical.

The resonator chamber 2 has the following dimensions, for example: diameter: 10 mm, length: 11 mm. The transducers 6 are made of a piezoelectric material, particularly a piezoelectric ceramic (e.g., barium-lead-zirconate), and have a thickness in the range from approximately 0.2 to 1.0 mm.

If at least one of the transducers 6 is electrically excited near its natural resonance, approximately plane soundwaves are emitted into the liquid 1, which are reflected at the opposite transducer. The thickness of the liquid layer (length of the resonator chamber 2) is selected in such a way that multiple liquid resonances occur in the range of the frequency characteristic of the transducers, at each of which a standing wave field is excited. The particular transducer not used for excitation is used to measure the amplitude and the frequency of the liquid resonances arising.

For performing the method described above, the excitation is performed using one of the transducers 6 at a frequency of 8 MHz, for example. The sequence of the liquid resonances $f_k$ (see FIG. 2) is registered using the opposite transducer, and the desired acoustic values are calculated from the deviations from the harmonic sequence of an ideal plane resonator having the same thickness of the liquid layer by adapting the simulation function (equations 4, 5) to the observed deviations of the liquid resonances.

An altered embodiment of a resonator arrangement having a multipart chamber body is shown in FIG. 4 in a partially cut away side view and in a cut away top view. The resonator chamber 2 is formed by a channel having a rectangular cross-section, in which the liquid 1 is located. The openings of the sample chamber 2 on both sides at the connection parts 3 allow the supply and removal of the liquid. Advantageously, measurements may be performed using this resonator arrangement in flow-through operation. Two diametrically opposite walls of the sample chamber 2 are formed by piezoelectric transducers 6, which correspond to the transducers 6 in the embodiment shown in FIG. 3. The remaining two opposite walls of the sample chamber 2 are formed by chamber bodies 4. The chamber bodies 4 each have a projection having a specific thickness, which is used as a spacer and an attachment body for the piezoelectric transducers 6. The chamber bodies 4 and the transducers 6 have the same length in the flow-through direction (alignment of the channel) and are terminated on each of the two sides by a cover plate 7. Openings having a rectangular cross-section are incorporated in each of the cover plates 7, which continue the cross-section of the liquid channel and/or the sample chamber 2. The plates 7 on both sides are connected to one another and to the chamber bodies 4 via fasteners 8 (e.g., screwed on). The construction made of chamber bodies 4, cover plate 7, fasteners 8, and transducers 6 forms a uniform resonator arrangement which is enclosed by a housing 9. This unit may preferably be installed in liquid lines in order to allow continuous performance of the measurement method described above. The acoustic parameters of the liquid obtained are used, for example, for process control in a facility in which the liquid is transported or processed.

The sample chamber 2 has the following dimensions, for example: length: 50 mm, cross-section: 20*10 mm. The parts of the resonator arrangement are made, for example, from corrosion-free steel or even from plastic.

The embodiment shown in FIG. 4 represents a resonator arrangement analogous to FIG. 3, in which a plane wave field is also generated. In both embodiments, the liquid 1 is in direct contact with the transducers 6. However, direct transducer contact is not a necessary feature of the invention. Rather, additional intermediate layers may also be provided between the liquid and the system which excites the liquid resonances. The intermediate layers are formed, for example, by electrode layers (metal layers) or even by additional layers to set a specific acoustic impedance of the resonator chamber. Additional layers are made, for example, of a suitable plastic.

In the embodiment of the present invention shown in FIG. 5, the resonator chamber 2 is formed by a tubular body. The tubular body preferably has a circular cross-section and is made of metal (e.g., gold). The resonator chamber 2 has multiple functions. Firstly, it receives the liquid sample 1 for measurement. Secondly, it represents the carrier for the piezoelectric transducers 6, which are attached to the outside of the tubular body. Finally, the resonator chamber 2 forms a shared ground electrode for both transducers 6. For the tubular body, fixing the tube on the outside of the wall between the two half cylinders in order to exclude cylindrical modes of the resonances is advantageous.

Confocal wave fields may be generated using the resonator arrangement shown in FIG. 5, which form approximately plane wave fields at sufficiently high harmonic orders. The cylinder resonator shown in FIG. 5 is preferably operated at an excitation frequency in which the natural resonance of the transducer 6 is coincident with a natural resonance (or one of its higher order waves) of the tubular body. A natural resonance of the overall arrangement then occurs when the soundwaves emitted by the transducer 6 into the tubular body 2 are reflected on the inner wall in such a way that they are superimposed nearly in phase on the emitted waves. To achieve this condition, the thickness of the tubular body is suitably selected for a given wall material of the tubular body. For example, a tubular body made of gold having an inner diameter of 7 mm and a thickness of 0.2 mm is used.

The tubular body may also be made of a different material, particularly plastic or ceramic. If the material is electrically insulating, an electrically conductive coating is produced on the surface of the tubular body to form the ground contacts for the transducers.

The features of the invention disclosed in the preceding description, the drawing, and the claims may be of significance both alone and in any combination for implementing the invention in its various embodiments.

The invention claimed is:

1. A method for determining acoustic parameters of a liquid in a resonator arrangement having a resonator chamber, comprising the steps of:

acoustic excitation of the liquid in the resonator chamber in such a way that a sequence of liquid resonances is excited in a frequency range in which a wall material of the resonator chamber or associated transducers have natural resonances with an amplitude different from zero, measurement of resonance frequencies of the liquid resonances in the resonator chamber, determining observed deviations of the measured resonance frequencies from ideal resonance frequencies in an ideal resonator corresponding to the resonator chamber, calculating a simulation function ($y_k$), depending on the acoustic parameters of the liquid, representing calculated deviations of the resonance frequencies from the ideal resonance frequencies with the simulation function ($y_k$), adapting the calculated deviations to the observed deviations through variation of acoustic parameter variables of the simulation function ($y_k$), and deriving the acoustic parameters sought from the adapted simulation function ($y_k$), and reporting storing or displaying said derived acoustic parameters.

2. The method according to claim 1, wherein the acoustic parameters comprise at least one of the speed of sound in the liquid, mass density of the liquid, and viscoelastic properties of the liquid.

3. The method according to claim 1, wherein plane standing soundwave fields are excited in the liquid.

4. The method according to claim 3, wherein the plane standing soundwave fields are generated using curved transducers, which are excited at high frequencies at a distance from the transducer basic frequency, or using plane transducers.

5. The method according to claim 1, wherein the simulation function ($y_k$) is formed by:

$$y_k = \frac{c_L}{2D}\left\{k + \frac{2}{\pi}\arctan\frac{z_L}{z_R\tan\left\{\pi\frac{f_k}{f_R}\right\}}\right\} \text{ for } f_k < f_R$$

and $$y_k = \frac{c_L}{2D}\left\{k - 2 + \frac{2}{\pi}\arctan\frac{z_L}{z_R\tan\left\{\pi\frac{f_k}{f_R}\right\}}\right\} \text{ for } f_k > f_R,$$

where
D is layer thickness of the liquid
k is harmonic order
$f_k$ is observed resonance frequency
$f_R$ is coupled resonance frequency of a reflecting wall structure
$c_L$ is speed of sound in the liquid
$Z_L$ is acoustic impedance of the liquid
$Z_R$ is acoustic impedance of the reflecting wall structure
$y_k$ is calculated deviation.

6. The method according to claim 1, wherein the simulation function is empirically determined through measurements using a liquid having known acoustic parameters.

7. The method according to claim 1, wherein the sequence of liquid resonances is formed by multiple sequential resonance frequencies of the liquid which lie in a neighborhood below a predetermined natural frequency of the resonator chamber, and an approximate value of a basic frequency of the liquid is determined from two or more neighboring resonance frequencies, whose difference is smaller than the natural frequency of the resonator chamber, to determine the observed deviation from the ideal resonance frequency.

8. The method according to claim 1, wherein the measurement of the resonance frequencies, the determination of the observed deviations, and the adaptation of the simulation function is performed multiple times and an average value of the particular adapted acoustic parameter is calculated.

9. The method according to one of the preceding claims, wherein the acoustic parameters of the liquid are detected while this liquid flows through the resonator chamber.

* * * * *